United States Patent [19]
Byrd

[11] Patent Number: 5,653,228
[45] Date of Patent: Aug. 5, 1997

[54] MEDICAL TUBE HOLDING DEVICE AND ASSOCIATED SECURING STRAP

[76] Inventor: Timothy N. Byrd, 1267 Old Cades Cove Rd., Townsend, Tenn. 37882

[21] Appl. No.: 567,930

[22] Filed: Dec. 6, 1995

Related U.S. Application Data

[63] Continuation-in-part of Ser. No. 516,817, Aug. 18, 1995, abandoned, which is a continuation-in-part of Ser. No. 328,685, Oct. 25, 1994, Pat. No. 5,448,985.

[51] Int. Cl.$^6$ ................................................ A62B 18/08
[52] U.S. Cl. ............................ 128/207.11; 128/207.17
[58] Field of Search ........................ 128/207.11, 207.17, 128/DIG. 15, DIG. 26

[56] References Cited

U.S. PATENT DOCUMENTS

| | | | |
|---|---|---|---|
| D. 310,721 | 9/1990 | Beisang, III | D24/49 |
| 3,046,989 | 7/1962 | Hill | 128/348 |
| 3,826,254 | 7/1974 | Mellor | 128/133 |
| 3,927,676 | 12/1975 | Schultz | 128/351 |
| 3,977,407 | 8/1976 | Coleman et al. | 128/348 |
| 4,018,221 | 4/1977 | Rennie | 128/185 |
| 4,088,136 | 5/1978 | Hasslinger | 128/349 R |
| 4,120,304 | 10/1978 | Moor | 128/348 |
| 4,142,527 | 3/1979 | Garcia | 128/348 |
| 4,249,529 | 2/1981 | Nestor et al. | 128/207.17 |
| 4,327,716 | 5/1982 | Ansted | 128/133 |
| 4,331,144 | 5/1982 | Wapner | 128/207.17 |
| 4,333,468 | 6/1982 | Geist | 128/348 |
| 4,351,331 | 9/1982 | Gereg | 128/207.17 |
| 4,367,735 | 1/1983 | Dali | 128/207.18 |
| 4,489,723 | 12/1984 | Simons et al. | 128/207.16 |
| 4,548,200 | 10/1985 | Wapner | 128/207.17 |
| 4,569,348 | 2/1986 | Hasslinger | 604/179 |
| 4,583,976 | 4/1986 | Ferguson | 604/174 |
| 4,617,017 | 10/1986 | Hubbard et al. | 604/179 |
| 4,671,787 | 6/1987 | Widman | 604/179 |
| 4,690,675 | 9/1987 | Katz | 604/177 |
| 4,744,358 | 5/1988 | McGinnis | 128/207.17 |
| 4,774,944 | 10/1988 | Mischinski | 128/207.17 |
| 4,799,923 | 1/1989 | Campbell | 604/179 |
| 4,822,342 | 4/1989 | Brawner | 604/180 |
| 4,823,789 | 4/1989 | Beisang, III | 128/207.18 |
| 4,836,200 | 6/1989 | Clark | 128/207.18 |
| 4,932,943 | 6/1990 | Nowak | 604/180 |
| 5,009,227 | 4/1991 | Nieuwstad | 128/207.17 |
| 5,037,397 | 8/1991 | Kalt et al. | 604/174 |
| 5,038,778 | 8/1991 | Lott | 128/207.17 |
| 5,042,477 | 8/1991 | Lewis | 128/207.17 |
| 5,135,506 | 8/1992 | Gentelia et al. | 604/180 |
| 5,163,914 | 11/1992 | Abel | 604/180 |
| 5,215,532 | 6/1993 | Atkinson | 604/180 |
| 5,306,233 | 4/1994 | Glover | 602/41 |
| 5,368,024 | 11/1994 | Jones | 128/207.17 |
| 5,448,985 | 9/1995 | Byrd | 128/207.17 |

OTHER PUBLICATIONS

Brit. J. Anaesth. (1955), 27, 260, "A New Endotracheal Catheter Fixation", by Frey.

*Primary Examiner*—Aaron J. Lewis
*Attorney, Agent, or Firm*—Pitts & Brittian, P.C.

[57] ABSTRACT

A medical tube holding device (10) for holding at least one medical tube (13) at a desired position proximate the body of a patient. The tube holding device (10) includes a tube engaging assembly (14) for releasably engaging and maintaining the position of at least one medical tube (13). The tube engaging assembly (14) has first and second strap engaging portions (18, 20) for engaging a securing strap (12). The securing strap (12) has a first end portion (24) secured to the first strap engaging portion (18) of the tube engaging assembly (14) and has a second end portion (25) secured to the second strap engaging portion (20) of the tube engaging assembly (14), and defines a cap-like configuration for being received over a convexed body portion to facilitated engagement of the securing strap (12) with a selected portion of the body of a patient as the securing strap (12) and the tube engaging assembly (14) cooperatively encircle the body of the patient.

11 Claims, 5 Drawing Sheets

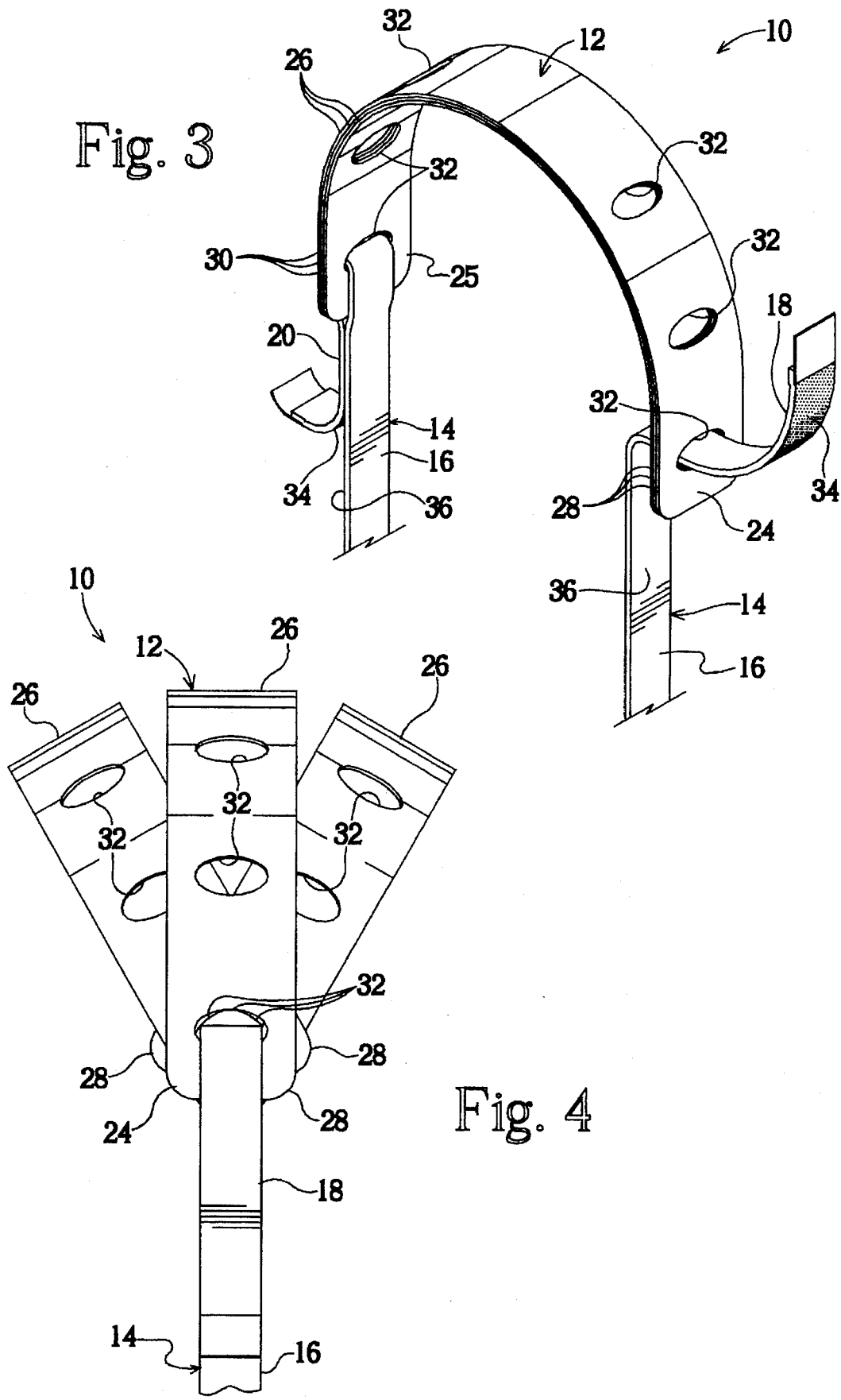

MEDICAL TUBE HOLDING DEVICE AND ASSOCIATED SECURING STRAP

This application is a continuation-in-part of my U.S. patent application Ser. No. 08/516,817, filed Aug. 18, 1995, now abandoned, which was a continuation-in-part of U.S. application Ser. No. 328,685, filed Oct. 25, 1994, now U.S. Pat. No. 5,448,985, issued on Sep. 12, 1995.

TECHNICAL FIELD

This invention relates to a medical tube holding device, and an associated securing strap, for securing at least one medical tube proximate the body of a patient. In this particular invention the tube holding device includes a tube engaging assembly and a securing strap which cooperatively encircle a selected portion of the body of a patient in order to engage and maintain the position of one or more medical tubes.

BACKGROUND ART

It is common in various medical procedures for tubes to be used to carry fluids to, or from, the body of a patient. For example, the use of endotracheal tubes to effect artificial ventilation of a patient's lungs is a common medical procedure, and various catheterization procedures involve the use of medical tubes to carry fluid to, or from, a patient. For many such procedures it is desirable, and in certain circumstances necessary, for the position of the medical tube to be stabilized. For example, inadvertent movement of an endotracheal tube can result in inadvertent removal of the tube from the body of the patient and/or discomfort to the patient. Because of the need to prevent inadvertent movement of medical tubes while in use, various tube holding devices have been designed to maintain the position of medical tubes. Many such devices have utilized securing straps which encircle a portion of the body of the patient to maintain the position of the holding device, with the holding device, in turn, engaging and maintaining the position of the medical tube. Various tube holding devices utilizing securing straps are disclosed in U.S. Pat. Nos. 5,042,477; 5,009,227; 4,836,200; 4,774,944; 4,744,358; 4,671,787; 4,617,017; 4,569,348; 4,548,200; 4,489,723; 4,367,735; 4,331,144; 4,249,529; 4,088,136; 4,018,221; and 3,927,676. However, such holding devices are prone to inadvertent slippage on the surface of the patient's body, particularly where the position of the tube and tube holder are such that the strap of the holding device must engage a convex surface, such as, for example, the back of the patient's head. Of course, slippage of the securing strap can result in a failure of the holding device to maintain the position of the medical tube, and may be the direct cause of movement of the tube.

Therefore, it is an object of the present invention to provide a medical tube holding device and an associated securing strap which efficiently maintain the position of one or more medical tubes.

It is another object of the present invention to provide a medical tube holding device and an associated securing strap which can be utilized to secure medical tubes at various locations proximate the body of a patient.

Yet another object of the present invention to provide a securing strap for a medical tube holding device which is not prone to slippage, even when the securing strap engages a convex body surface.

Still another object of the present invention is to provide a medical tube holding device and an associated securing strap which are easy to use and which are durable yet inexpensive to manufacture.

SUMMARY OF THE INVENTION

The present invention provides a medical tube holding device, and an associated securing strap, for holding one or more medical tubes in a desired position proximate the body of a patient. The tube holding device includes a tube engaging assembly for releasably engaging and maintaining the position of at least one medical tube, and for partially encircling a selected portion of the body of the patient. The tube engaging assembly has first and second strap engaging portions for engaging the securing strap such that the tube engaging assembly and securing strap encircle a selected portion of the body of the patient to facilitate the holding of the medical tube(s) in the desired position. In this regard, the securing strap has a first end portion secured to the first strap engaging portion of the tube engaging assembly, and has a second end portion secured to the second strap engaging portion of the tube engaging assembly. The securing strap also including a plurality of strap members having first and second end portions. The strap members are secured together proximate their first end portions and secured together proximate their second end portions such that the strap members pivot with respect to one another proximate the first and second end portions of the strap members. This pivoting engagement of the strap members allows the strap members to be pivoted into a cap-like configuration which facilitates the engagement of the securing strap with a selected portion of the body of a patient, thereby insuring that the tube engaging assembly is maintained in the desired position, and, in turn, insuring that any medical tubes secured in the tube engaging assembly are maintained in the desired position. However, in an alternate embodiment the securing strap is fixed, or integrally formed, in the cap-like configuration rather than being constructed of pivoting strap members.

BRIEF DESCRIPTION OF THE DRAWINGS

The above mentioned features of the invention will be more clearly understood from the following detailed description of the invention read together with the drawings in which:

FIG. 3 illustrates a partial perspective view of a tube holding device of the present invention.

FIG. 4 illustrates a partial side elevation view of a tube holding device of the present invention.

BEST MODE FOR CARRYING OUT THE INVENTION

Figure 1:
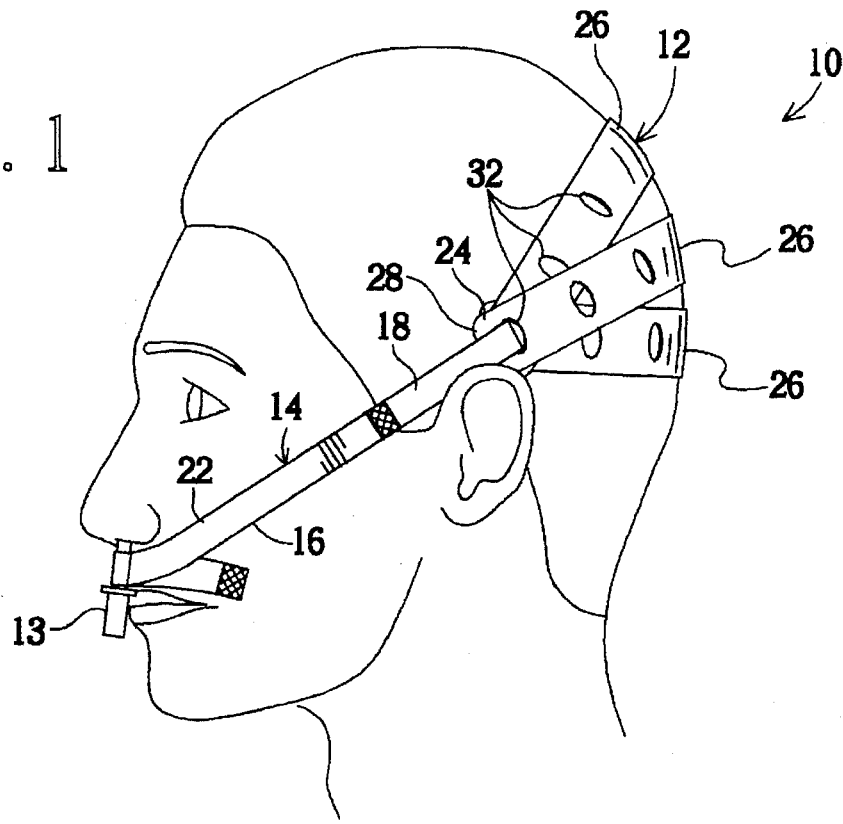
FIG. 1 illustrates a side elevation view of a tube holding device of the present invention.
Figure 2:
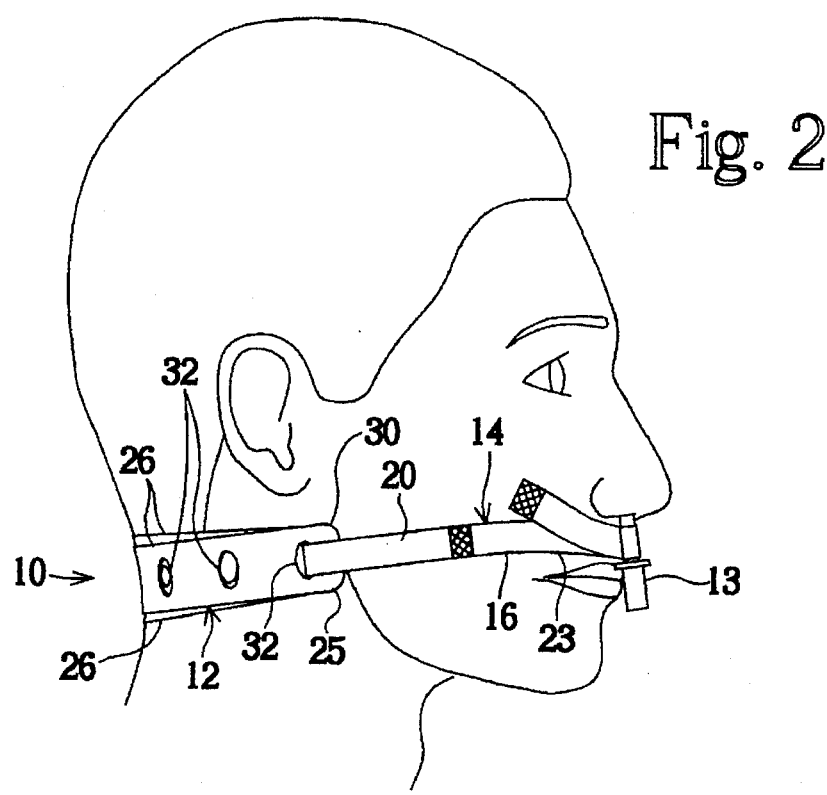
FIG. 2 illustrates a side elevation view of a tube holding device of the present invention.
Figure 5:
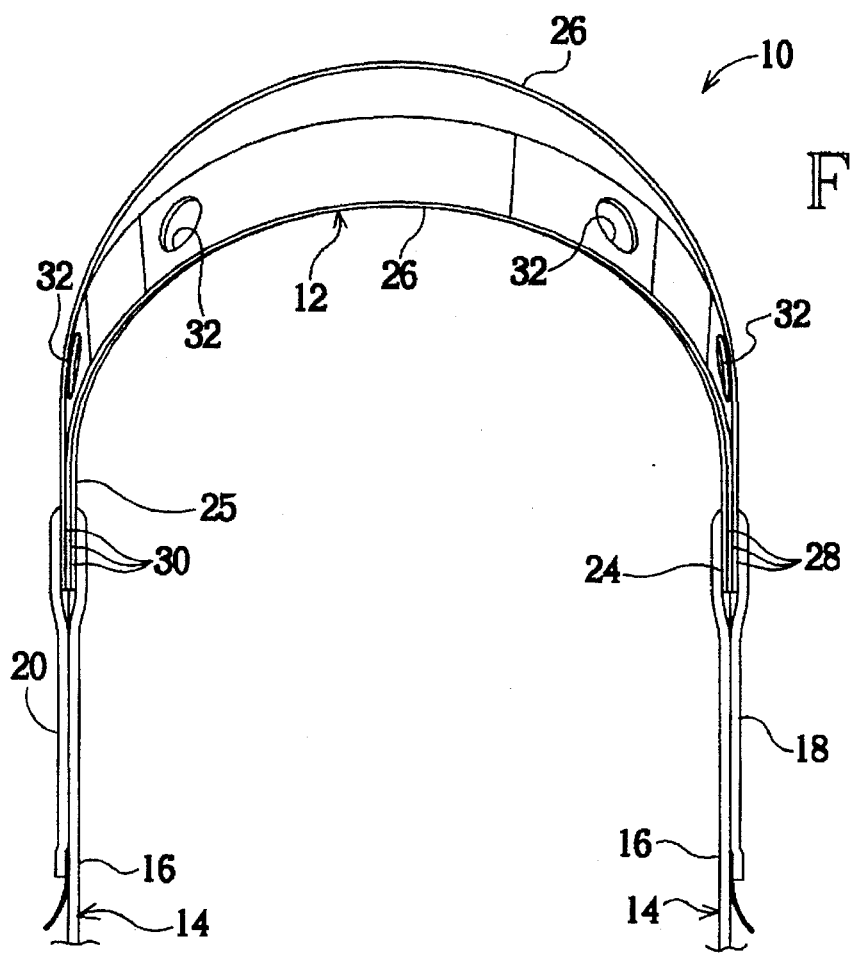
FIG. 5 illustrates a partial front elevation view of a tube holding device of the present invention.

A medical tube holding device incorporating various features of the present invention is illustrated at 10 in FIGS.

1–6, and an associated securing strap incorporating various features of the present invention is illustrated at 12 in FIGS. 1–6. In the illustrated embodiment, the device 10 is depicted as securing the position of an endotracheal tube 13 as such endotracheal tube 13 is receive in the nasal passageway of the patient. However, it will be understood that the tube holder 10 can be use to secure the position of various types of medical tubes, at various locations proximate the body of a patient.

The tube holding device 10 includes at least one tube engaging assembly 14 having a body 16, and having first and second strap engaging portions 18 and 20 which serve to engage the securing strap 12 such that the tube engaging assembly 14 and the securing strap 12 encircle a selected portion of the body of a patient. The tube engaging assembly 14 includes a tube engaging mechanism for releasably engaging one or more medical tubes 13 in order to releasably secure the position of such tubes. In the illustrated embodiment of FIGS. 1–2, the tube engaging mechanism includes a first tube engaging apparatus 22 and a second tube engaging apparatus 23 which adhesively engage one or more tubes as described in U.S. Pat. No. 5,448,985, issued Sep. 12, 1995. However, it will be recognized by those skilled in the art that the tube engaging assembly 14 can incorporate various tube engaging mechanisms, and the illustrated apparatus 22 and 23 are merely illustrative of one preferred mechanism.

The securing strap 12 defines a first end portion 24 for being secured to the first tube engaging portion 18 of the tube engaging assembly 14 and a second end portion 25 for being secured to the second tube engaging portion 20. In the preferred embodiment of FIGS. 1–6, the securing strap 22 includes a plurality of elongated strap members 26, each of which defines a first end portion 28 and a second end portion 30. In the illustrated embodiment three such strap members 26 are shown, but it is contemplated that two, or more than three strap members 26, can be used if desired. Preferably the strap members 26 are fabricated of a soft resilient material. For example, one preferred fabricating material is a spun-bond polypropylene material, which is soft, breathable, inexpensive, and comfortable to the patient. However, other suitable materials can be used if desired.

As best illustrated in FIG. 3, the securing strap 12 is constructed such that the first end portions 28 of the strap members 26 overlay one another and are pivotally secured together. Similarly, the second end portions 30 of the strap members 26 overlay one another and are pivotally secured together. It will be recognized that by securing the end portions 28 and 30 of the strap members 26 such that the strap members 26 pivot with respect to one another allows the strap members 26 to be pivoted into a cap-like configuration whereby the central portions of the strap members 26 are selectively spaced. In this selectively spaced disposition, the securing strap 12 can conform to selected portions of the body, such as, for example, the back of the patient's head where a convex surface is defined, and where a single, narrow strap member would not serve to hold the position of the tube holding device (See FIG. 1). As a consequence, the stable positioning of the tube engaging assembly 14 is facilitated, and the possibility of inadvertent movement of any tubes 13 secured by the tube engaging assembly 14 is reduced. Moreover, the central portions of the strap members 26 can be pivoted together when necessary to accommodate placement of the strap 12 at alternate locations on the body of a patient. For example, in FIG. 2, the securing strap 12 is received about the neck of the patient where little, or no, spacing of the strap members 26 is required. Thus, it will be appreciated that the pivoted spacing of the strap members 26 can be varied as required depending upon the location at which the securing strap 12 engages the body of the patient.

In the preferred embodiment the pivotal securing of the first end portions 28 and the second end portions 30 is accomplished by the securing mechanism which secures the first and second strap engaging portions 18 and 20 of the assembly 14 to the securing strap 12. More specifically, each of the strap members 26 is provided with at least one opening 32 at its first end portion 28 for receiving therethrough the first strap engaging portion 18 of the assembly 14, and at least one opening 32 at its second end portion 30 for receiving therethrough the second strap engaging portion 20 of the assembly 14. Once the first and second strap engaging portions 18 and 20 have been received through the openings 32 in the first and second end portions 28 and 30, respectively, the strap engaging portions 18 and 20 are secured to the body 16 of the assembly 14 at selected points to form loops in the body 16 which serve to secure the first and second strap engaging portions 18 and 20 of the assembly 14 to the first and second end portions 28 and 30, respectively, of the strap members 26. Further, the securing of the assembly 14 to the strap members 26 by looping the first and second strap engaging portions 18 and 20 through the openings 32 in the strap members pivotally secures the first end portions 28 of the strap members 26 together, and pivotally secures the second end portions 30 of the strap members 26 together.

Figure 6:
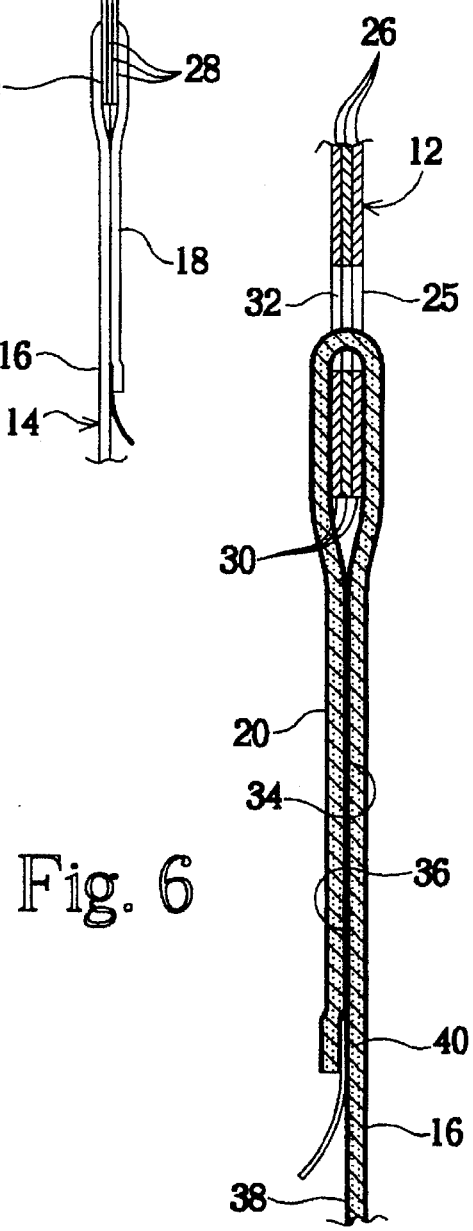
FIG. 6 illustrates a partial front elevation view, in section, of a tube holding device of the present invention.

In the preferred embodiment the first and second strap engaging portions 18 and 20 are each provided with an adhesive surface portion 34 for releasably securing the first and second strap engaging portions 18 and 20 to a selectively spaced portion of the body 16 after such strap engaging portions have been looped through the openings 32. (See FIG. 3) In order to facilitate the releasable engagement of the adhesive surfaces portions 34 with selectively spaced portions of the body 16, in the preferred embodiment a smooth, substantially non-porous surface 36 is defined along at least a portion of the body 16. In this regard, in the preferred embodiment the body 16 includes an outer layer 38 of cellophane or plastic which provides the surface 36 as best illustrated in FIG. 6. It will also be noted that in the preferred embodiment the body 16 defines a core 40 which is fabricated from a foam material, such as 1772 foam tape manufactured by 3M®, disposed between layers of cellophane or plastic, such that the body 16 is strong and durable, yet soft and flexible to facilitate the comfort of the patient. Whereas, in the illustrated embodiment the adhesive surface portions 18 and 20 are used, it is contemplated that other mechanisms, such as hook and loop fasteners can be used if desired.

In the preferred embodiment of the device 10 the effective length of the tube engaging assembly 14, and the effective length of the securing strap 12, are adjustable. In this regard, by selectively altering the position at which the strap engaging portions 18 and 20 engage the body 16 after being received through the openings 32 in the strap members 26, the effective length of the assembly 14 can be altered. Further, in the preferred embodiment, each of the strap members 26 is provided with a plurality of openings 32 which are selectively spaced along the length of the strap members 26. Thus, by selecting the desired openings 12 for receiving the strap engaging portions 18 and 20 of the assembly 14 the effective length of the securing strap 12 can be altered.

Figure 7:
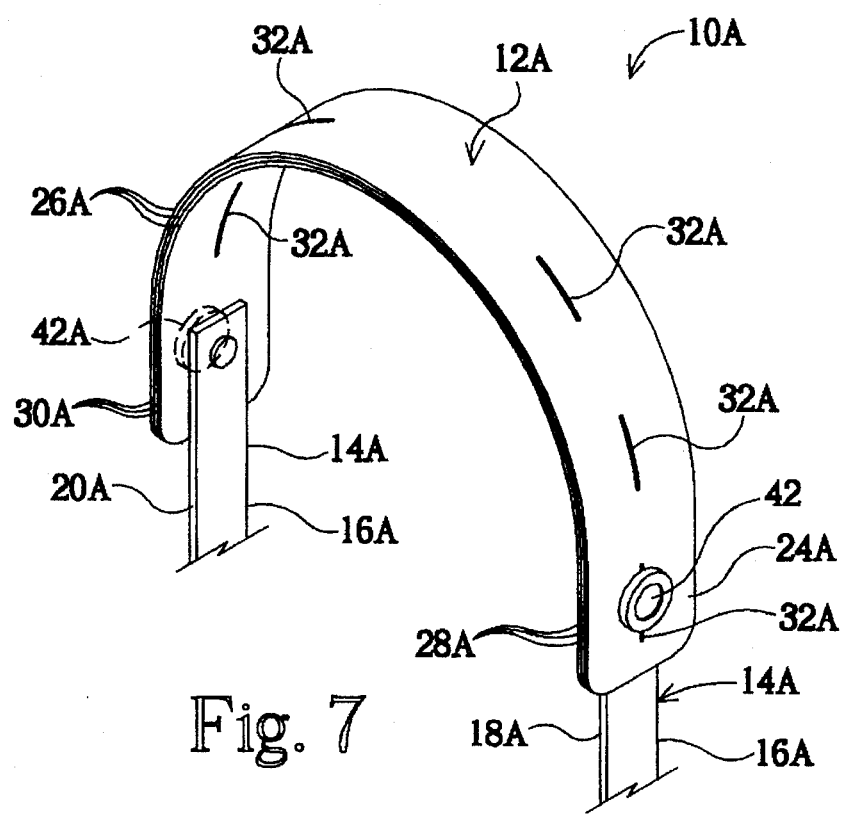
FIG. 7 illustrates a partial perspective view of an alternate embodiment of a tube holding device of the present invention.

Whereas FIGS. 1–6 illustrate one preferred mechanism for securing the securing strap 12 to the tube engaging assembly 14 to allow the strap members to pivot with respect to one anther, other mechanisms can be used. For example, in FIG. 7 an alternate embodiment of the tube holding device is illustrated at 10A. For convenience, features of the device 10A which are common to the above described device 10 are referenced with common numerals followed by the alphabetic character "A". In this embodiment the strap engaging portions 18A and 20A are provided with button members 42 which are releasably received through the openings 32A provided in the strap members 26A.

Figure 8:
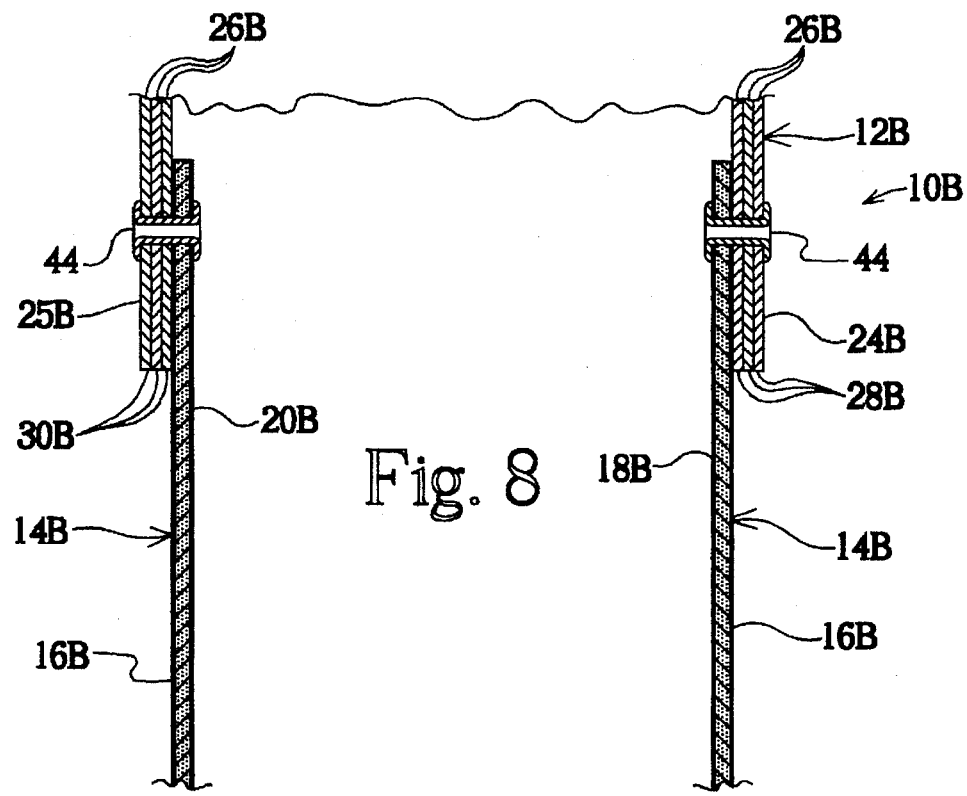
FIG. 8 illustrates a partial front elevation view, in section, of a further alternate embodiment of a tube holding device of the present invention.

Another example of a tube holding device with an alternate securing mechanism is illustrated in FIG. 8 and referenced at 10B. For convenience, features of the device 10B which are common to the above described device 10 are referenced with common numerals followed by the alphabetic character "B". It will be noted that in the embodiment of FIG. 8 the end portions 28B of the straps 26B are secured to the strap engaging portion 18B of the assembly 14B with a rivet 44, and the end portions 30B of the strap members 26B are secured to the strap engaging portion 20B of the assembly 14B with a further rivet 44. Of course, other mechanical fasteners can be used and the rivets 44 are simply illustrative of one suitable fastener.

Figure 9:
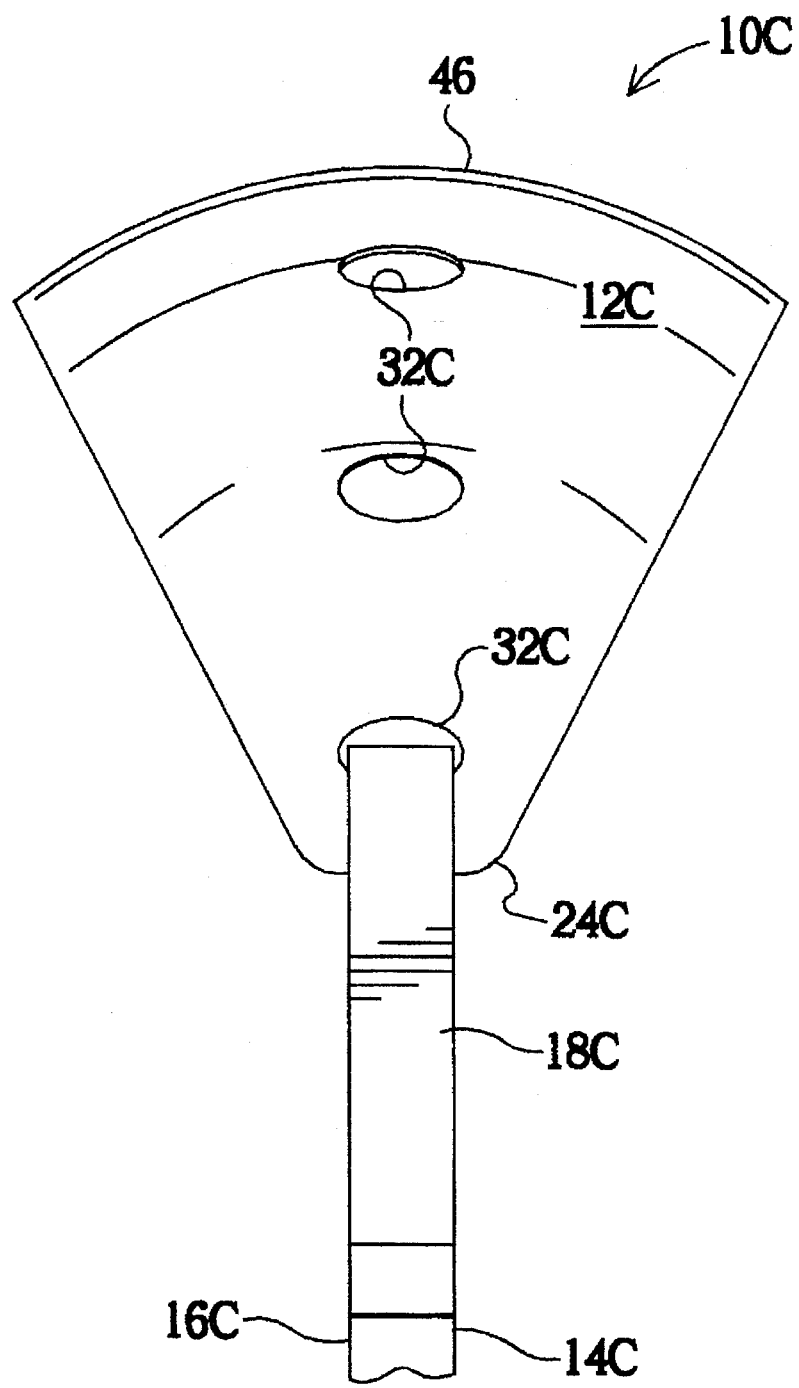
FIG. 9 illustrates a partial perspective view of yet another alternate embodiment of a tube holding device of the present invention.

Whereas in the preferred embodiment it is contemplated that the strap members 26 are separate members which are secured proximate their opposite ends so as to pivot with respect to one another to selectively define a cap-like configuration, it is also contemplated that the position of the strap members 26 can be fixed in the cap-like configuration if desired. Further, an alternate embodiment of the tube holding device is illustrated at 10C in FIG. 9 wherein an integral cap-like portion 46 is utilized rather than a plurality of separate strap members. It will be noted that the cap-like portion 46 is provided with openings 32C for receiving the strap engaging portions 18C and 20C of the assembly 14C, but, as with the previously described embodiments, other securing mechanisms can be used to secure the tube engaging assembly 14C to the securing strap 12C.

In light of the above it will be recognized that the present invention provides a medical tube holding device and an associated securing strap having great advantages over the prior art. The tube holding device is releasably securable to various parts of a patient's body and the securing strap, with its pivoting strap members, insures the stable positioning of the tube holding device and the medical tubes secured therein. However, while a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. A medical tube holding device for holding at least one medical tube proximate a patient's body, said tube holding device comprising:

a tube engaging assembly for releasably engaging and maintaining the position of at least one medical tube, said tube engaging assembly having first and second strap engaging portions; and a securing strap for releasably maintaining the position of said tube engaging assembly, said securing strap having a first end portion secured to said first strap engaging portion of said tube engaging assembly and having a second end portion secured to said second strap engaging portion of said tube engaging assembly, said securing strap including at least three strap members each having a first and second end portion and a central portion, said strap members being pivotally secured together proximate said first end portions of said strap members and pivotally secured together proximate said second end portions of said strap members such that said strap members pivot with respect to one another proximate said first and second end portions of said strap members, whereby said strap members can be pivoted to selectively space said central portions of said strap members to facilitated engagement of said securing strap with a selected portion of a patient's body as said securing strap and said tube engaging assembly cooperatively encircle a selected portion of a patient's body.

2. The tube holding device of claim 1 wherein said first end portions of said strap members are pivotally secured to one another to form said first end portion of said securing strap, and said second end portions of said strap members are pivotally secured to one another to form said second end portion of said securing strap.

3. The tube holding device of claim 2 wherein said first end portion of said securing strap is pivotally secured to said first strap engaging portion of said tube engaging assembly, and said second end portion of said securing strap is pivotally secured to said second strap engaging portion of said tube engaging assembly.

4. The tube holding device of claim 2 wherein said first end portion of each said strap member defines at least one opening for receiving therethrough said first strap engaging portion of said tube engaging assembly, and said first strap engaging portion is provided with a securing mechanism for securing said first strap engaging portion of said tube engaging assembly to a selected portion of said tube engaging assembly after said first strap engaging portion is received through said openings in said first end portions of said strap members, whereby said first end portions of said strap members are pivotally secured together and said first end portions of said strap members are pivotally secured to said first strap engaging portion of said tube engaging assembly, and wherein said second end portion of each said strap member defines at least one further opening for receiving therethrough said second strap engaging portion of said tube engaging assembly, and said second strap engaging portion is provided with a securing mechanism for securing said second strap engaging portion of said tube engaging assembly to a selected portion of said tube engaging assembly after said second strap engaging portion is received through said further openings in said second end portions of said strap members, whereby said second end portions of said strap members are pivotally secured together, and said second end portions of said strap members are pivotally secured to said second strap engaging portion of said tube engaging assembly.

5. The medical tube holding device of claim 3 wherein said first end portion of each said strap member is provided with at least one opening, and said first strap engaging portion of said tube engaging assembly includes a button member for being received through said openings in said first end portions of said strap members, whereby said first end portions of said strap members are pivotally secured together and said first end portions of said strap members are pivotally secured to said first strap engaging portion of said tube engaging assembly, and wherein said second end portion of each said strap member is provided with at least one further opening, and said second strap engaging portion of said tube engaging assembly includes a further button member for being received through said further openings in said second end portions of said strap members, whereby said second end portions of said strap members are pivotally secured together and said second end portions of said strap members are pivotally secured to said second strap engaging portion of said tube engaging assembly.

6. A medical tube holding device for holding at least one medical tube proximate a patient's body, said tube holding device comprising:

a tube engaging assembly for releasably engaging and maintaining the position of at least one medical tube, said tube engaging assembly having first and second strap engaging portions, said first strap engaging portion being provided with an adhesive surface portion adapted for securing said first strap engaging portion of said tube engaging assembly to a selected portion of said tube engaging assembly, said second strap engaging portion being provided with an adhesive surface portion adapted for securing said second strap engaging portion of said tube engaging assembly to a selected portion of said tube engaging assembly; and a securing strap for releasably maintaining the position of said tube engaging assembly, said securing strap having a first end portion releasably secured to said first strap engaging portion of said tube engaging assembly and having a second end portion releasably secured to said second strap engaging portion of said tube engaging assembly, said securing strap including at least one strap member having first and second end portions and a central portion, said first end portion of said strap member defining at least one opening for receiving therethrough said first strap engaging portion of said tube engaging assembly, whereby said adhesive surface portion of said first strap engaging portion is secured to a selected portion of said tube engaging assembly after said first strap engaging portion is received through said opening in said first end portion of said strap member, whereby said first end portion of said strap member is pivotally secured to said first strap engaging portion of said tube engaging assembly, said second end portion of said strap member defining at least one further opening for receiving therethrough said second strap engaging portion of said tube engaging assembly, whereby said adhesive surface portion of said second strap engaging portion is secured to a selected portion of said tube engaging assembly after said second strap engaging portion is received through said further opening in said second end portion of said strap member, whereby said second end portion of said strap member is pivotally secured to said second strap engaging portion of said tube engaging assembly.

7. The medical tube holding device of claim 6 wherein said strap member is provided with a plurality of said openings selectively spaced along a portion of the length of said strap member and wherein said strap member is provided with a plurality of said further openings selectively spaced along a portion of the length of said strap member.

8. The medical tube holding device of claim 6 wherein each said strap member is provided with a plurality of said openings selectively spaced along a portion of the length of said strap member and wherein each said strap member is provided with a plurality of said further openings selectively spaced along a portion of the length of said strap member.

9. A medical tube holding device for holding at least one medical tube proximate a patient's body, said tube holding device comprising:

a tube engaging assembly for releasably engaging and maintaining the position of at least one medical tube, said tube engaging assembly having first and second strap engaging portions, said first strap engaging portion being provided with an adhesive surface portion adapted for securing said first strap engaging portion of said tube engaging assembly to a selected portion of said tube engaging assembly, said second strap engaging portion being provided with an adhesive surface portion adapted for securing said second strap engaging portion of said tube engaging assembly to a selected portion of said tube engaging assembly; and a securing strap for releasably maintaining the position of said tube engaging assembly, said securing strap having a first end portion secured to said first strap engaging portion of said tube engaging assembly and having a second end portion secured to said second strap engaging portion of said tube engaging assembly, said securing strap including at least three strap members each having a first and second end portion and a central portion, said strap members being pivotally secure together proximate said first end portions of said strap members to form said first end portion of said securing strap and pivotally secured together proximate said second end portions of said strap members to form said second end portion of said securing strap such that said strap members pivot with respect to one another proximate said first and second end portions of said strap members, whereby said strap members can be pivoted to selectively space said central portions of said strap members to facilitated engagement of said securing strap with a selected portion of a patient's body as said securing strap and said tube engaging assembly cooperatively encircle a selected portion of a patient's body, said first end portion of each said strap member defining at least one opening for receiving therethrough said first strap engaging portion of said tube engaging assembly, whereby said adhesive surface portion of said first strap engaging portion is secured to said selected portion of said tube engaging assembly after said first strap engaging portion is received through said openings in said first end portions of said strap members, whereby said first end portions of said strap members are pivotally secured together and said first end portions of said strap members are pivotally secured to said first strap engaging portion of said tube engaging assembly, said second end portion of each said strap member defining at least one further opening for receiving therethrough said second strap engaging portion of said tube engaging assembly, whereby said adhesive surface portion of said second strap engaging portion is secured to said selected portion of said tube engaging assembly after said second strap engaging portion is received through said further openings in said second end portions of said strap members, whereby said second end portions of said strap members are pivotally secured together and said second end portions of said strap members are pivotally secured to said second strap engaging portion of said tube engaging assembly.

10. The medical tube holding device of claim 9 wherein said securing mechanism of said first strap engaging portion includes an adhesive for bonding said first strap engaging portion to said selected portion of said tube engaging assembly, and wherein said securing mechanism of said second strap engaging portion includes an adhesive for bonding said second strap engaging portion to said further selected portion of said tube engaging assembly.

11. The medical tube holding device of claim 10 wherein said adhesive of said securing mechanism of said first strap engaging portion is provided along a selected portion of a surface of said first strap engaging portion, and wherein said adhesive of said securing mechanism of said second strap engaging portion is provided along a selected portion of a surface of said second strap engaging portion.

* * * * *